United States Patent [19]

Leight et al.

[11] Patent Number: 4,819,624
[45] Date of Patent: Apr. 11, 1989

[54] BANDED EARPLUG

[76] Inventors: Howard S. Leight, 3945 Ridgemont Dr.; Charles Leight, 3511 Shoreheights Dr., both of Malibu, Calif. 90265; Frederic A. Leight, 8210 Bobby-Boyar St., Canoga Park, Calif. 91304

[21] Appl. No.: 64,173
[22] Filed: Jun. 18, 1987
[51] Int. Cl.⁴ ............................................. A61F 11/00
[52] U.S. Cl. ..................................... 128/866; 128/152
[58] Field of Search ................................. 128/151, 152

[56] References Cited

U.S. PATENT DOCUMENTS

| 997,673 | 7/1911 | Hegge | 128/152 |
|---|---|---|---|
| 1,279,396 | 9/1918 | Michelson et al. | 128/152 |
| 2,246,737 | 6/1941 | Knudsen | 128/152 |
| 2,888,921 | 6/1959 | Nielson et al. | 128/151 |
| 3,080,011 | 3/1963 | Henderson | 128/151 |
| 3,301,253 | 1/1967 | Glorig | 128/152 |
| 4,122,841 | 10/1978 | Rock et al. | 128/151 |
| 4,434,794 | 3/1984 | Leight . | |
| 4,461,290 | 7/1984 | Gardner, Jr. et al. | 128/152 |
| 4,490,857 | 1/1985 | Leight et al. | 128/152 |
| 4,671,265 | 6/1987 | Andersson | 128/151 |

FOREIGN PATENT DOCUMENTS

| 3536793 | of 0000 | German Democratic Rep. | 128/152 |
|---|---|---|---|
| 1355052 | of 0000 | United Kingdom | 128/152 |

Primary Examiner—Robert A. Hafer
Assistant Examiner—Charles H. Sam
Attorney, Agent, or Firm—Freilich, Hornbaker, Rosen & Fernandez

[57] ABSTRACT

Earplug assemblies are provided for mounting at the ends of a resilient band, which readily deform to tightly seal to the walls of the ear that surround the entrance to the ear canal. Each assembly includes a shell having a closed forward end that presses against the ear and an open rear end that receives an armature mounted on the band. The shell has a front end tapered at a large angle such as 90°, while the armature has a forward portion tapered at a small angle such as 20°, to leave an air gap between the forward portions of the shell and armature. With the forward tip of the armature pressing against the center of the shell front, outer portions of the shell front can deflect rearwardly and radially inwardly into the air gap.

5 Claims, 1 Drawing Sheet

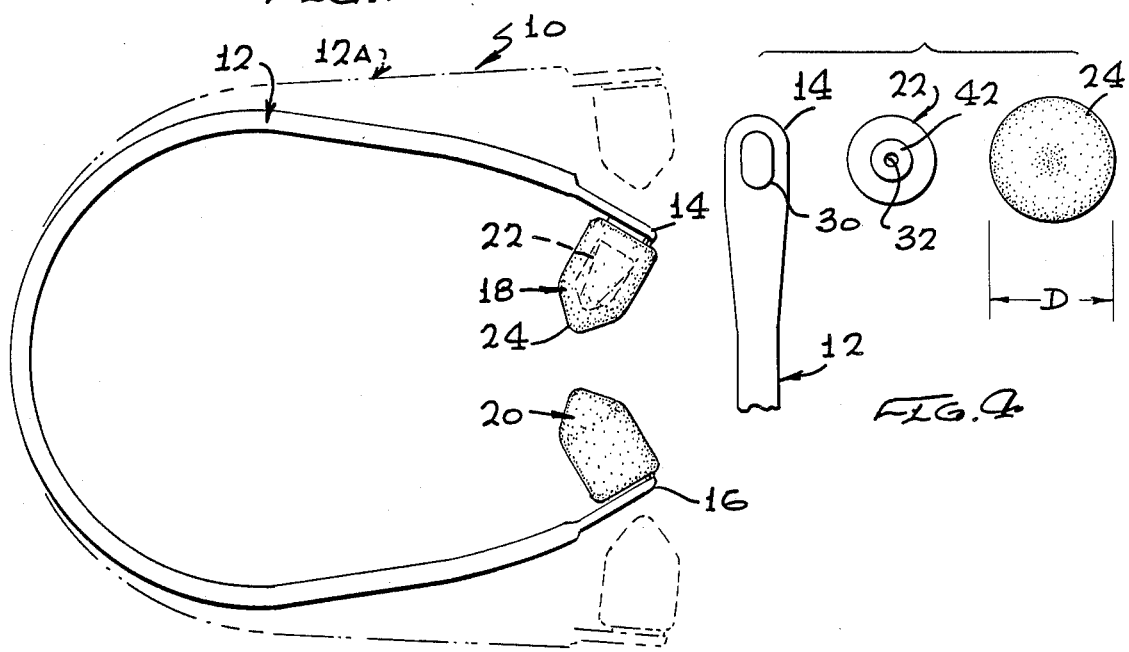
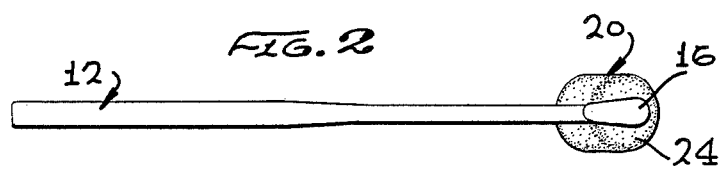
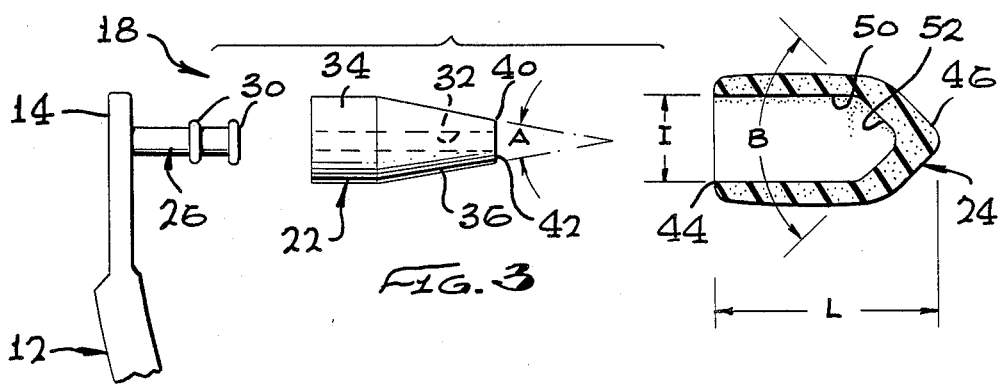
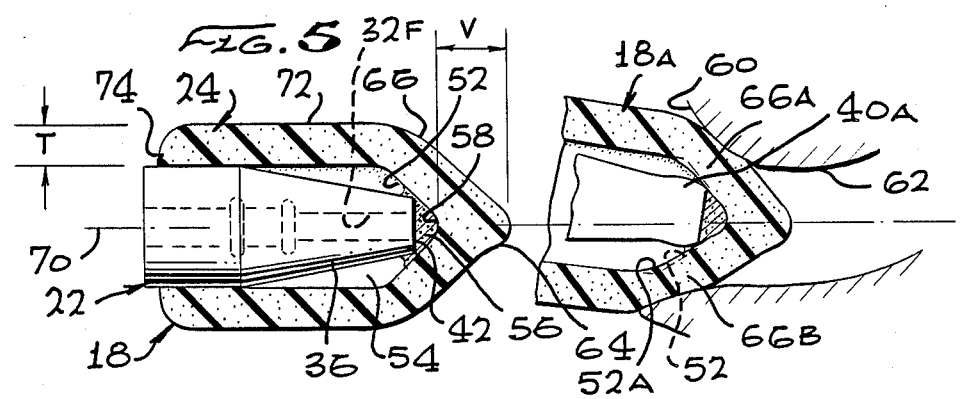

BANDED EARPLUG

BACKGROUND OF THE INVENTION

There are two commonly used approaches to sealing the ears of people against loud sounds such as occur in factories. One approach is to provide an earplug with most of it entering the ear canal, and which holds itself in position by friction between the earplug and the ear canal of the wearer. Another approach is to mount earplug assemblies at the ends of a band that extends halfway about the wearer's head, with each earplug assembly sealing against the walls of the ear which surround the entrance to the ear canal. The band approach avoids objections of some people to the insertion of objects in their ear canal. However, unlike the ear canal, which is largely cylindrical and more easily sealed against, the walls surrounding the entrance to the ear canal are of a more irregular shape. A band earplug which could be constructed at relatively low cost, and which tightly sealed to the walls around the entrance to the ear canal of a wearer, would be of considerable value.

SUMMARY OF THE INVENTION

In accordance with one embodiment of the present invention, a band earplug is provided which effectively seals against the walls of a wearer's ear which surrounds the entrance to his ear canal. The band earplug includes a pair of earplug assemblies mounted at the opposite ends of the band, each assembly including an armature mounted on a band end and a soft body or shell mounted on the armature. Each armature has a rearward portion closely received in the shell, a forward end or tip which supports the tip of the shell, and a forward portion which is tapered at a small angle to leave an air gap between the outer portion of the front of the shell and the armature. The front end of the shell is tapered at an angle much larger than that of the armature front portion. Rearward and radially inward pressure on the front end of the shell can be accommodated by the air gap.

Both the shell and the armature are formed of soft resilient foam. The armature has a hole which receives a mounting post on the band end. The forward end of the shell has a projecting nose that facilitates centering of the shell forward end on the ear canal.

The novel features of the invention are set forth with particularity in the appended claims. The invention will be best understood from the following description when read in conjunction with the accompanying drawings.

BRIEF DESCRIPTION OF THE DRAWINGS

FIG. 1 is a plan view of a band earplug constructed in accordance with the present invention.

FIG. 2 is a side elevation view of the band earplug of FIG. 1.

FIG. 3 is an exploded side view of a portion of the band earplug of FIG. 1.

FIG. 4 is an exploded front view of the elements of FIG. 3.

FIG. 5 is an enlarged view showing how an earplug assembly of the present invention seals to the ear of a wearer.

DESCRIPTION OF THE PREFERRED EMBODIMENT

FIG. 1 illustrates a band earplug 10 of the present invention, which includes a band 12 that fits halfway around the head of a person, and which has ends 14, 16 that lie opposite the wearer's ears. The band is resilient, and when it is expanded to the configuration 12A, it urges a pair of earplug assemblies 18, 20 mounted at the band ends against the ears of the wearer. Each assembly such as 18 includes an armature 22 that is held to the earplug end and a body or shell 24 that surrounds the armature and that directly presses against the wearer's ear.

As shown in FIG. 3, the band end includes a mounting post 26 having enlargements 30 thereon. The armature 22 has a central hole 32 which receives the mounting post in interference therewith, so the armature is secured on the band end. The armature has a substantially cylindrical rear portion 34 mounted on the band and a tapered front portion 36 which is tapered at a relatively small angle A to have a progressively smaller diameter at progressively more forward locations. The armature forward portion has a smallest diameter at its front end 40 which ends in a tip 42. The shell 24 has an open rear end 44 and a closed front end 46. The shell has a largely cylindrical hole 50 which closely receives the rearward portion 34 of the armature. The front end 46 of the shell and the inside surface 52 of the shell hole at its front end are tapered by a large angle B of about 90°. This taper angle is much larger, and preferably more than twice, the taper angle A of the front portion of the armature, where A is about 20°. As a result, when the armature is fully inserted into the shell, with the tip 42 of the armature lying at the front of the shell hole, there is an air gap formed between the surfaces 52, 36.

FIG. 5 shows the assembled armature 22 and shell 24, showing the air gap 54 which lies around the front portion 36 of the armature, and showing the tip 42 of the armature lying closely behind the center of the shell front end. It may be noted that a drop of resilient adhesive 56 is used to join the front end and tip 42 of the armature to the center front of the shell at its inside 58. The armature tip supports the shell front end primarily through adhesive.

The earplug assembly 18 presses with a force of about six ounces against the walls 60 of the wearer's ear that surround and form the entrance to the wearer's ear canal 62. In order to guide the front end of the assembly towards engagement with the ear walls, the front end of the shell is formed with a middle or center 64 that is in the form of a bulge. While the thickness T of the shell is generally about 3 mm, the thickness V behind the bulge is about 4.5 mm. The front end of the shell also includes a radially outer portion 66, spaced from the shell and earplug axis 70, that is substantially uniformally tapered at an angle of about 90°.

When the armature 22 pushes the shell at 18A against the outer walls of the ear canal, the outer portion 66 of the shell front end is deformed as at 66A and 66B. Such deformation is easily accomplished because the shell is of soft foam material, and because the outer portion 66 of the shell can deflect radially inwardly towards the axis 70 and rearwardly, because the air gap 54 lies behind it. The change in air gap configuration can be seen by comparing the original configuration 52 to the deformed configuration 52A. The armature 22, also being formed of soft foam material, can also deflect to accommodate deflection of the shell, to allow the shell to closely fit against the walls surrounding the entrance to the ear canal. The forward end 32F of the armature hole is devoid of the rigid post 26 and of any other rigid material, so the front end of the armature is very easily deflected sidewardly and rearwardly, as shown at 40A.

A majority of the volumes of both the armature and shell are occupied by gas bubbles or cells. Although the outer portion 66 of the shell front and the middle or intermediate portion 72 of the shell can deflect, the shell is stabilized by the fact that the center of its front end at 58 and 64 is backed by the tip of the armature (through the adhesive 58), and by the fact that the rear 74 of the shell is positioned by the cylindrical rear portion 34 of the armature. The rear 74 of the shell can slide with respect to the armature rear portion 34, to accommodate rear shell deflection by the walls of the wearer's ear. Also, air from the air gap 54 can pass out between the armature rear 34 and the shell. Applicant prefers to leave the rear end 34 of the armature with a slick outside surface, while the tapered portion 36 ncan be left rough.

One design of band earplug that applicant has constructed includes shells of an outer diameter D (FIG. 4) of 18 mm and a length L (FIG. 3) of 27 mm. The diameter D is much larger than the diameter of the human ear canal (external auditory metus) which is about 7 mm. The inside diameter I of the shell hole was 11 mm.

Thus, the invention provides a band earplug which is easily constructed and effectively seals against the walls of the ear which surround the entrance to the ear canal. Each earplug assembly includes an armature with a tapered forward portion, which is tapered at a smaller angle than the front of the shell hole to leave an air gap around the tapered armature portion. The shell can deform into this air gap, while the tip of the shell is supported against rearward movement and the rear of the shell is slideably positioned.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A band earplug comprising:
a band with opposite ends, which fits about halfway around the head of a person with said ends lying opposite the ears of the person, said band constructed to urge said opposite ends towards each other to press towards the person's ears;
a pair of earplug assemblies, each including an armature coupled to one of said band ends and a shell of soft resilient material mounted on the armature;
said shells have substantially open rear ends and closed front ends, and each armature projects through the open rear end of a shell and has a front armature end lying behind the front of the shell to help support the shell front end against rearward deflection;
the front end of each of said shells having a center which can enter the outer end of the person's ear canal and an outer portion that is designed to press against the walls of the ear that surround the entrance to the ear canal, the diameter of said outer portion being too great to enter the ear canal of a person even when pressed against the walls around the entrance of a person's ear canal;
each corresponding armature and shell constructed with the armature supporting the center of the front end of the shell against rearward deflection, but with an air gap between the outer portion of the shell front end and the armature to allow the outer portion to be deflected when it presses against the ear walls that surround the entrance to the ear canal;
each earplug shell front end has an extreme front end at said center, and said shell front end is tapered to have a progressively smaller diameter at locations progressively closer to said extreme front end, at both the inside and outside of the shell; and
each armature has a tapered front portion which has a smaller taper angle than the inside of said shell tapered front end, to form said air gap.

2. A band earplug comprising:
a band with opposite ends, which fits about halfway around the head of a person with said ends lying opposite the ears of the person, said band constructed to urge said opposite ends towards each other to press towards the person's ears;
a pair of earplug assemblies, each including an armature coupled to one of said band ends and a shell of soft resilient material mounted on the armature;
said shells have substantially open rear ends and closed front ends, and each armature projects through the open rear end of a shell and has a front armature end lying behind the front of the shell to help support the shell, each armature having a substantially cylindrical rear end and each shell having a substantially cylindrical inside surface which closely surrounds the armature rear end but which can slide thereon and which can pass air between them;
the front end of each of said shells having a center which can enter the outer end of the person's ear canal and an outer portion that is designed to press against the walls of the ear that surround the entrance to the ear canal, the diameter of said outer portion being too great to enter the ear canal of a person even when pressed against the walls around the entrance of a person's ear canal;
each corresponding armature and shell constructed with the armature supporting the center of the front end of the shell against rearward deflection, but with an air gap between the outer portion of the shell front end and the armature to allow the shell outer portion to be deflected when it presses against the ear walls that surround the entrance to the ear canal.

3. The band earplug described in claim 2 wherein:
the diameter of said outer portion of said shell is at least about 18 milimeters, whereby to prevent entrance into a human ear canal.

4. A band earplug comprising:
a band with opposite ends, which fits about halfway around the head of a person with said ends lying opposite the ears of the person, said band constructed to urge said opposite ends towards each other to press towards the person's ears;
a pair of earplug assemblies, each including an armature coupled to one of said band ends and a shell of soft resilient material mounted on the armature;
said shells have substantially open rear ends and closed front ends, and each armature projects through the open rear end of a shell and has a front armature end lying behind the front of the shell to help support the shell front end against rearward deflection;

the front end of each of said shells having a center which can enter the outer end of the person's ear canal and an outer portion that is designed to press against the walls of the ear that surround the entrance to the ear canal, the diameter of said outer portion being too great to enter the ear canal of a person even when pressed against the walls around the entrance of a person's ear canal;

each corresponding armature and shell being constructed with the armature supporting the center of the front end of the shell against rearward deflection, each armature having a tapered front portion and there being an air gap between the armature tapered front portion and the outer portion of the shell front end to allow the outer portion of the shell to be easily deflected when it presses against the ear walls that surround the entrance to the ear canal.

5. The band earplug described in claim 4 wherein:

each earplug shell front end is tapered to have a progressively greater diameter at locations progressively farther from the center of the shell front end;

the tapered front portion of each armature has a smaller taper angle than the inside of each shell tapered front end.

* * * * *